(12) United States Patent
Lohitharn

(10) Patent No.: US 12,043,857 B2
(45) Date of Patent: *Jul. 23, 2024

(54) ENHANCED PRODUCTION OF RHAMNOLIPIDS USING AT LEAST TWO CARBON SOURCES

(71) Applicant: Stepan Company, Northfield, IL (US)

(72) Inventor: Nattaporn Lohitharn, Palatine, IL (US)

(73) Assignee: Stepan Company, Northfield, IL (US)

( * ) Notice: Subject to any disclaimer, the term of this patent is extended or adjusted under 35 U.S.C. 154(b) by 49 days.

This patent is subject to a terminal disclaimer.

(21) Appl. No.: 17/472,979

(22) Filed: Sep. 13, 2021

(65) Prior Publication Data

US 2021/0403969 A1 Dec. 30, 2021

Related U.S. Application Data

(62) Division of application No. 16/048,945, filed on Jul. 30, 2018, now Pat. No. 11,142,782.

(60) Provisional application No. 62/538,830, filed on Jul. 31, 2017.

(51) Int. Cl.
C12P 19/44 (2006.01)
C12P 7/64 (2022.01)

(52) U.S. Cl.
CPC .............. *C12P 19/44* (2013.01); *C12P 7/64* (2013.01)

(58) Field of Classification Search
CPC ................................. C12P 19/44; C12P 7/64
See application file for complete search history.

(56) References Cited

U.S. PATENT DOCUMENTS

| | | | |
|---|---|---|---|
| 4,628,030 A | 12/1986 | Kaeppeli | |
| 4,933,281 A | 6/1990 | Lacy | |
| 5,501,966 A | 3/1996 | Gianni | |
| 5,658,793 A | 8/1997 | Gianni | |
| 7,202,063 B1 | 4/2007 | Gunther | |
| 9,884,883 B2 | 2/2018 | Lohitharn | |
| 10,144,943 B2 | 12/2018 | Lohitharn | |
| 11,142,782 B2* | 10/2021 | Lohitharn | C12P 19/44 |
| 2013/0130319 A1 | 5/2013 | Schaffer et al. | |
| 2016/0326561 A1* | 11/2016 | Lohitharn | C12P 19/44 |
| 2018/0222934 A1 | 8/2018 | Lohitharn | |

FOREIGN PATENT DOCUMENTS

| | | |
|---|---|---|
| CN | 101173238 | 5/2008 |
| CN | 103589765 | 2/2014 |
| CN | 104312942 | 1/2015 |
| CN | 104498526 | 4/2015 |
| CN | 106987545 | 7/2017 |
| KR | 1020130084760 | 7/2013 |
| WO | 2016179249 | 11/2016 |

OTHER PUBLICATIONS

European Patent Office, Extended European Search Report, European Patent Application No. 18841379, mailed Apr. 19, 2021, 17 pages.

Lee et al. "Production of Rhamnolipid Biosurfactant by Fed-batch Culture of Pseudomonas aeruginosa Using Glucose as a Sole Carbon Source," Biosci. Biotechnol. Biochem., vol. 63, No. 5, 1999, pp. 946-947.

Matsufuji et al. "High production of rhamnolipids by Pseudomonas aeruginosa growing on ethanol," Biotechnology Letters, vol. 19, Dec. 1997, pp. 1213-1215.

Avili et al. "Comparison between batch and fed-batch production of rhamnolipid by Pseudomonas aeruginosa," Iranian Journal of Biotechnology, vol. 10, No. 4, Oct. 2012, pp. 263-269.

Banat et al. "Cost effective technologies and renewable substrates for biosurfactants' production," Frontiers in Microbiology vol. 5, Dec. 12, 2014.

Banat et al. "Microbial biosurfactants production, applications and future potential", Appl Microbiol Biotechnol vol. 87, 2010, pp. 427-444.

Chen et al. "Repeated pH-stat fed-batch fermentation for rhamnolipid production with indigenous pseudomonas aeruginosa S2," Appl Microbiol Biotechnol vol. 76, 2007, pp. 67-74.

Daverey et al., "Kinetics of Growth and Enhanced Sophorolipids Production by Candida bombicola Using a Low-Cost Fermentative Medium," Appl Biochem Biotechnol vol. 160, 2010, pp. 2090-2101.

Desai et al., "Microbial Production of Surfactants and Their Commercial Potential," Microbiology and Molecular Biology Reviews, vol. 61, No. 1, Mar. 1997, pp. 47-64.

George, "Microbial Production of Biosurfactants," PhD Thesis, Mahatma Ghandi University, India, Nov. 2010, 291 pages.

Gong et al., "Rhamnolipid production, characterization and fermentation scale-up by Pseudomonas aeruginosa with plant oils," Biotechnol Lett vol. 37, 2015, pp. 2033-2038.

Gudina et al., "Valorization of agro-industrial wastes towards the production of rhamnolipids," Bioresource Technology, vol. 212, 2016, pp. 144-150.

Heyd, "Continous production of rhamnolipids by means of process intergration," PhD. Dissertation, Institut fur Technische Chemie Bereich Wasser-und Geotechnologie Forschungszentrum Karlsruhe, 2009.

Kaskatepe et al., "Rhamnolipid Biosurtactants Produced by *Pseudomonas* Species," Brazilian Archives of Biology and Technology vol. 59, Jan.-Dec. 2016, pp. 1-16.

Li et al., "Rhamnolipid Production by Pseudomonas aeruginosa GIM 32 Using Different Substrates Including Molasses Distillery Wastewater," Appl Biochem Biotechnol, Sep. 10, 2010.

McNeil et al., "Practical fermentation technology," John Wiley & Sons Ltd., England, 2008.

Mendes et al., "Physicochemical Properties of Rhamnolipid Biosurfactant from Pseudomonas aeruginosa PA1 to Applications in Microemulsions," Journal of Biomaterials and Nanobiotechnology, vol. 6, Jan. 2015, pp. 64-79.

(Continued)

*Primary Examiner* — Vera Afremova

(74) *Attorney, Agent, or Firm* — McAndrews, Held & Malloy, Ltd.

(57) ABSTRACT

Provided is a method for improving the yield of rhamnolipids comprising culturing in medium containing a triglyceride containing oil and sweetener as a carbon source.

12 Claims, 1 Drawing Sheet

(56) References Cited

OTHER PUBLICATIONS

Muller et al., "Rhamnolipids—Next generation surfactants?," Journal of Biotechnology, vol. 162, Jun. 2012, pp. 366-380.
Neto et al., "Production of rhamnolipids in solid-state cultivation:Characterization, downstream processing and application in the cleaning of contaminated soil," Biotechnology Journal, vol. 4, 2009, pp. 748-755.
Nitschke et al., "Rhamnolipids and PHAs: Recent reports on Pseudomonas-derived molecules of increasing industrial interest," Process Biochemistry, vol. 46, 2011, pp. 621-630.
Onbasli et al., "Biosurfactant production in sugar beet molasses by some *Pseudomonas* spp.," Journal of Environmental Biology, vol. 30, No. 1, Jan. 2009, pp. 161-163.
Patel et al., "Biosurfactant production by Pseudomonas aeruginosa GS3 from molasses," Letters in Applied Microbiology, vol. 25, 1997, pp. 91-94.
Pornsunthorntawee et al., "Biosurfactant production by Pseudomonas aeruginosa SP4 using sequencing batch reactors: Effects of oil loading rate and cycle time," Bioresource Technology, vol. 100, 2009, pp. 812-818.
Randhawa et al., "Rhamnolipid biosurfactants—past, present, and future scenario of global market," Frontiers in Microbiology vol. 5, Sep. 2, 2014, pp. 1-7.
Rashedi et al., "Environmental importance of rhamnolipid production from molasses as a carbon source," Int. J. Enviorn Sci Tech., vol. 2, No. 1, Spring 2005, pp. 59-62.
Rahman et al., "Production of rhamnolipid Biosurfactants by Pseudomonas aeruginosa DS10-129 in a microfluidic bioreactor," Biotechnology and Applied Biochemistry vol. 55, 2010, pp. 45-52.
Wang et al., "Engineering Bacteria for Production of Rhamnolipid as an Agent for Enhanced Oil Recovery," Biotechnology and Bioengineering vol. 98, May 7, 2007, pp. 842-853.
Wittgens et al., "Growth independent rhamnolipid production from glucose using the non-pathogenic Pseudomonas putida KT2440," Microbial Cell Factories vol. 10, Oct. 17, 2011, pp. 80-98.
Zhu et al., Enhanced rhamnolipids production by Pseudomonas aeruginosa based on a pH stage-controlled fed-batch fermentation process, Bioresource Technology vol. 117, 2012, pp. 208-213.
International Searching Authority, International Search Report and Written Opinion, Application No. PCT/US2018/044329, dated Nov. 16, 2018, 12 pages.
Europe Patent Office, Supplementary European Search Report, Application No. 16789993.9, dated Jan. 8, 2019, 13 pages.
International Bureau, International Preliminary Report on Patentability, Application No. PCT/US2016/030721, dated Nov. 7, 2017, 8 pages.
International Searching Authority, International Search Report and Written Opinion, Application No. PCT/US2016/030721, dated Aug. 12, 2016, 11 pages.
Ito et al., "Lipase Production in Two-Step Fed-Batch Culture of Organic Solvent-Tolerant Pseudomonas aeruginosa LST-03," Journal of Bioscience and Bioengineering, vol. 91, No. 3, 2001, pp. 245-250.
Haba et al., "Screening and production of rhamnolipids by Pseudomonas aeruginosa 47T2 NCIB 40044 from waste frying oils," Journal of Applied Microbiology, vol. 88, 2000, pp. 379-387.
Japan Patent Office, Office Action, Application No. 2020-505135, Apr. 26, 2022, 3 pages.
Japan Patent Office, Office Action, Application No. 2020-505135, Nov. 29, 2022, 5 pages.

* cited by examiner

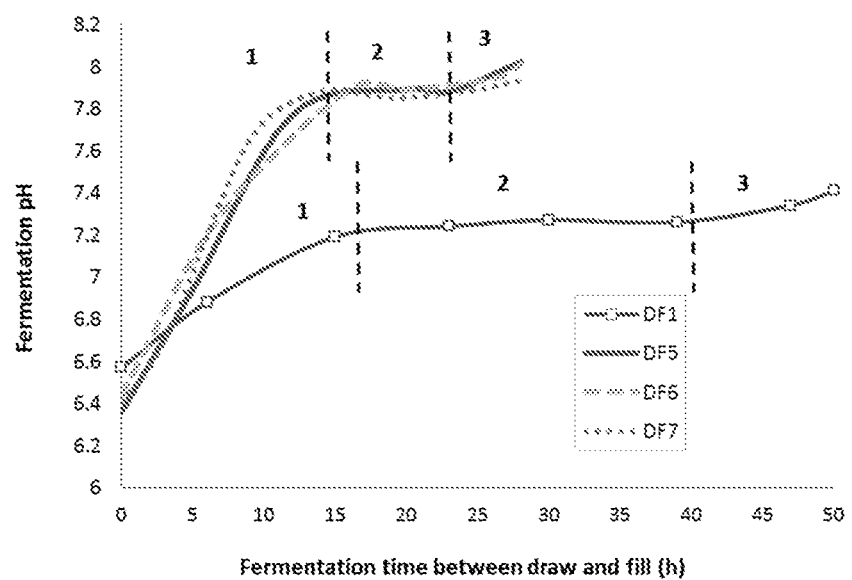

ENHANCED PRODUCTION OF RHAMNOLIPIDS USING AT LEAST TWO CARBON SOURCES

RELATED APPLICATIONS

The present application is a continuation of U.S. patent application Ser. No. 16/048,945, filed Jul. 30, 2018, now U.S. Pat. No. 11,142,782, which claims the benefit of and priority to U.S. Provisional Application No. 62/538,830, filed Jul. 31, 2017.

TECHNICAL FIELD

Provided is an improved method for producing rhamnolipids (RLs) comprising culturing a rhamnolipid producing microorganism in a medium comprising at least two carbon sources, in particular, a triglyceride containing oil and sweetener.

BACKGROUND

Due to increasing environmental concerns, bio-surfactants have gained much attention to public and consumers. One of the most sought after bio-surfactants are rhamnolipids (RL) because they have high ability to foam, clean, disperse, emulsify and lower surface tensions [1, 2]. Rhamnolipids are interface-active glycolipids containing carbohydrates (rhamnose) and aliphatic acids (hydroxy fatty acids). They contain one (monorhamnosylipids or monorhamnolipids) or two rhamnose units (dirhamnosylipids or di-rhamnolipids) and one or two (predominantly two) 3-hydroxy fatty acid residues. Rhamnolipids are predominantly produced by an aerobic fermentation of *Pseudomonas aeruginosa*. Other *Pseudomonas* species and *E. coli* have also been reported to produce rhamnolipids but their yields have a much lower titer and productivity than *P. aeruginosa* [3].

In order for rhamnolipids (RL) to compete with petroleum based synthesized surfactants such as sodium laureth sulfate (SLES) and sodium lauryl sulfate (SLS or SDS), the RL production cost has to come down significantly. Process optimization and fermentation performance are among the main cost drivers. A number of approaches including different feedstock, genetically modified strains and fermentation strategies have been carried out to increase the RL productivity and titer. Banat et al. [4] and Kaskatepe et al.[5] have extensive reviews on the production of biosurfactant using low cost feedstock (i.e., waste stream from agricultures and various industries). Since rhamnolipids contain arhamnose (sugar) moiety and 3-hydroxy fatty acid tail, several researchers have tried using molasses as a sole carbon feedstock. None of them have shown the rhamnolipid concentration >6 g/L with molasses concentration from 2-10% [6-9]. Vegetable oil, on the other hand, has been used to produce rhamnolipid at a higher concentration compared to the molasses feedstock. None have combined both feedstocks for the RL production thus far. A summary of the fermentation performance for RL production with vegetable oil is shown in Table 1.

TABLE 1

Fermentation performance of *P. aeruginosa* with different types of vegetable oil

| Carbon Source | Fermentation type | RL concentration (g/L) | Fermentation time (h) | RL productivity (g/L/h) | Reference |
|---|---|---|---|---|---|
| Soybean oil | Fed-batch | 95 | 216 | 0.44 | [10] |
| Corn oil | Batch | 27 | 120 | 0.23 | [11] |
| Palm oil | Batch | 71 | 144 | 0.49 | [12] |
| Sunflower oil | Batch | 27 | 72 | 0.38 | [11] |
| Soybean oil | Fed-batch | 65 | 90 | 0.72 | [13]* |

*pH control at 7-7.5 at the first 24 h then at 6-6.5 after

Although the U.S. Pat. No. 5,501,966 [10] claimed a fed-batch process producing RL as high as 112 g RL/L at 11 days (264 h) of fermentation and thus, the calculated RL productivity is only 0.42 g RL/L/h which is considered low. The productivity (g RL/L/h) is a very important process parameter since it represents how fast the rhamnolipids can be produced from a certain fermentation volume. The higher the RL productivity, the cheaper the RL production cost.

SUMMARY

Provided is a means to enhance the rhamnolipid production by introducing an addition of a sweetener (e.g., an unrefined sweetener or sugar) to an oil containing medium or long chain triglycerides (e.g., coconut oil or vegetable oil) or a combination of the two oils and thus, reducing the de novo synthesis of rhamnoses from fatty acids. This results in a shorter fermentation time and thus, an enhancement in RL productivity (g RL/L/h).

Also provided is a semi-continuous method for producing a plurality of fermentations comprising one or more rhamnolipids (RL) comprising: (a) culturing a rhamnolipid producing microorganism in culture medium comprising at least two carbon sources, wherein at least one carbon source is a sweetener and at least one carbon source is an oil containing medium or long chain triglycerides, at least one nitrogen source, at least one phosphorous source, at least one magnesium source, at least one potassium source, at least one sulfur source, at least one chloride source, and at least one sodium source for at least about 1 day and more particularly between about 1 to about 4 days, even more particularly between about 1 to about 3 days and yet even more particularly between about 1 to about 2 days to obtain a first fermentation medium comprising one or more rhamnolipids (RL) and one or more rhamnolipid producing microorganisms, yielding RL at a ratio of at least about 1.5 g RL/L/h, particularly, about 1.7 g RL/L/h and more particularly at least about 1.8 g RL/L/h and even more particularly yielding between about 1.8 g RL/L/h to about 3.0 g RL/L/h and yet even more particularly between about 1.8 g RL/L/h to about 2.7 g RL/L/h; (b) removing at least about 70% of said first fermentation medium obtained in (a), which in a particular embodiment, occurs during agitation and while maintaining air flow, where in a particular embodiment, said airflow is maintained with oxygen enriched air, in a container containing said fermentation medium; (c) replacing said first fermentation medium removed in (b) with culture medium having the composition set forth in step (a) and (d) repeating steps (a)-(c) at least one time to obtain a subsequent fermentation comprising rhamnolipids, wherein said steps (a)-(c) are capable of being repeated for at least about 20 days and more particularly for at least about 30 days.

In one embodiment, the method may further comprise adding a composition comprising one or more micronutrients at a concentration of 0.1-0.2% v/v of total fermentation volume per day. In yet another particular embodiment, at least about 40 g RL/L is obtained using said method. In yet another particular embodiment, 50 g RL/L is obtained; in an even more particular embodiment, at least about 55 g RL/L is obtained; in yet another particular embodiment, at least about 60 g RL/L is obtained; in an even more particular embodiment, at least about 65 g RL/L is obtained; in yet even more particular embodiment, at least about 70 g RL/L is obtained; in an even yet more of a particular embodiment, at least about 80 g RL/L is obtained; in an even yet more of a particular embodiment, at least about 90 g RL/L is obtained. In an even more particular embodiment between about 40 g RL/L and 110 g RL/L are obtained.

Also provided is a method for producing one or more rhamnolipids comprising culturing a rhamnolipid producing microorganism in culture medium comprising at least two carbon sources, wherein at least one carbon source is an unrefined sweetener and at least one carbon source is a vegetable oil, at least one nitrogen source, at least one phosphorous source, at least one magnesium source, at least one potassium source, at least one sulfur source, at least one chloride source, at least one sodium source and optionally at least one emulsifier for at least about 1 day which yields a titer of at least about 40 g RL/L, more particularly at least about 50 g RL/L; even more particularly, at least about 55 g RL/L; yet even more particularly, at least about 60 g RL/L; yet even more particularly, at least about 70 g RL/L; even yet more particularly, at least about 80 g RL/L; even yet more particularly, at least about 90 g RL/L is obtained or alternatively between about 40 g RL/L to about 110 g RL/L and/or at a rate of at least about 1.5 g RL/L/h. The method may further comprise isolating said rhamnolipid(s) from said rhamnolipid containing fermentation medium. In a particular embodiment, the culture medium is micronutrient free. This culture medium may be used in a semi-continuous fermentation, particularly the semi-continuous method set forth above, as well as batch and fed batch fermentations. The rhamnolipids may be isolated and purified using methods known in the art (see, for example, the U.S. Pat. No. 9,884,883. and U.S. application Ser. No. 15/611,045, filed Jun. 1, 2017).

Definitions

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges and are also encompassed within the invention, subject to any specifically excluded limit in the stated range. Where the stated range includes one or both limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this disclosure are incorporated by reference in their entirety. Nothing herein is to be construed as an admission that the invention is not entitled to antedate such disclosure by virtue of the prior invention. To the extent the material incorporated by reference contradicts or is inconsistent with this specification, the specification will supersede any such material.

It must be noted that as used herein and in the appended claims, the singular forms "a", "and" and "the" include plural references unless the context clearly dictates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention. Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. Thus, the terms "comprising", "including," containing", "having" etc. shall be read expansively or open-ended and without limitation. When used herein, the term "comprising" can be substituted with the term "containing" or sometimes when used herein with the term "having".

As defined herein, a "sweetener" is a substance that sweetens an edible product.

As defined herein, "an unrefined sweetener" is a sweetener containing water and sugar as a by-product of sugar processing but has not undergone the refining process It can also be extracted directly from including but not limited to sap, roots (e.g., potatoes, sweet potatoes, beets, particularly sugar beets), nectars, flowers, leaves, fruits, cane, trees, stalks.

As defined herein, a "refined sweetener" is a sweetener which has undergone a refining process using methods known in the art.

As defined herein, an "emulsifier" is an emulsifier is a type of surfactant typically used to keep emulsions (metastable mixtures of immiscible fluids) well dispersed. Emulsifiers typically have a hydrophobic (water-fearing) and a hydrophilic (water-loving) moiety. In an emulsion involving an oil and water, emulsifiers will surround the oil with their hydrophobic moiety oriented toward the oil, thus forming a protective layer so that the oil molecules cannot coalesce. This action helps keep the dispersed phase in small particles and preserves the emulsion. Emulsifiers may be anionic, nonionic, or cationic.

As defined herein, "a medium chain triglyceride" contains between fatty acids having an aliphatic tail of 6-12 carbon atoms.

As defined herein, "a long chain triglyceride" contains fatty acids having an aliphatic tail of more than 13 carbon atoms.

A defined herein, a "vegetable oil" contains mixtures of triglycerides derived from a plant or part thereof.

As defined herein, a "rhamnolipid" refers to a glycolipid that has a lipid portion that includes one or more, typically linear, saturated or unsaturated β-hydroxy-carboxylic acid moieties and a saccharide portion of one or more units of rhamnose. The saccharide portion and the lipid portion are linked via a β-glycosidic bond between the 1-OH group of a rhamnose moiety of the saccharide portion and the 3-OH group of a β-hydroxy-carboxylic acid of the lipid portion. Thus the carboxylic group of one carboxylic acid moiety defines the end of the rhamnolipid. Where more than one rhamnose-moiety is included in a rhamnolipid, each of the rhamnose moieties not linked to the lipid portion is linked to another rhamnose moiety via a 1,4 β-glycosidic bond. In embodiments where two or more β-hydroxy-carboxylic acids are present in a rhamnolipid, the β-hydroxy-carboxylic acid moieties are selected independently from each other. β-hydroxy carboxylic acid moieties of a respective plurality of β-hydroxy carboxylic acid moieties may in some embodiments be identical. In some embodiments they are different from each other.

As defined herein, a "micronutrient composition" is a composition comprising a micronutrient present in an amount no more than about 20 mg/L.

The terms "culture medium", "fermentation medium" are synonymous and are used interchangeably.

BRIEF DESCRIPTION OF THE FIGURES

FIG. 1 shows a pH trends of fermentation with and without molasses addition change.

DETAILED DESCRIPTION

Provided herein is an improved method for producing rhamnolipids. In a particular embodiment, the rhamnolipid may have the structure (I).

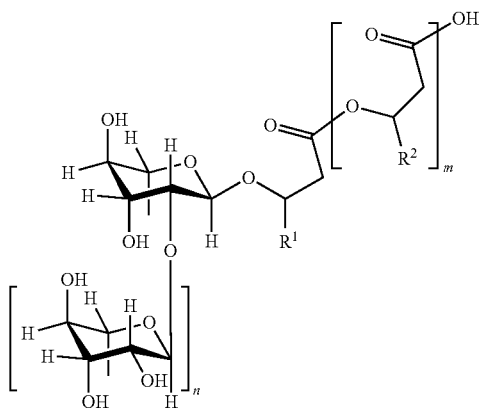

Where m=2, 1 or 0, in particular 1 or 0, n=1 or 0, or in particular 1, $R^1$ and $R^2$=independently of one another identical or different organic radical with 2 to 24, preferably 5 to 13, carbon atoms, in particular optionally branched, optionally substituted, in particular hydroxyl-substituted, optionally unsaturated, in particularly optionally mono-, di- or triunsaturated, alkyl radical, preferably one selected from the group consisting of pentenyl, heptenyl, nonenyl, undeceny and tridecenyl and $(CH_2)_o$—$CH_3$ where o=1 to 23, preferably 4 to 12.

Both the main chain as well as the branches may furthermore contain heteroatoms as for instance N, O, S, Se or Si or a carbon atom may be replaced by one of these heteroatoms. An aliphatic moiety may be substituted or unsubstituted with one or more functional groups. Substituents may be any functional group, as for example, but not limited to, amino, amido, carbonyl, carboxyl, hydroxyl, nitro, thio and sulfonyl.

Rhamnolipid Producing Microorganism

As noted above, the method comprises culturing a rhamnolipid producing microorganism. A rhamnolipid producing microorganism may be a host cell producing rhamnolipids. A recombinant host cell producing rhamnolipids may be a host cell, such as a bacterial cell that expresses a RhlA gene or ortholog thereof and/or a RhlB gene or ortholog thereof, and/or a RhlC gene or ortholog thereof, and/or RhlR gene or ortholog thereof, and/or RhlI gene or ortholog thereof, and/or RhlG gene or ortholog thereof and others.

Alternatively, a "rhamnolipid-producing microorganism" may be any microorganism, such as bacteria, which has the capacity to synthesize/produce rhamnolipids under suitable conditions which includes but is not limited to bacterium of the phyla Actinobacteria, Fimicutes and Proteobacteria. In a particular embodiment, the rhamnolipid-producing microorganism is a bacterium of the Gammaproteobacteria class. In a further embodiment, the rhamnolipid-producing microorganism is a bacterium of the Pseudomonalales order. In yet another further embodiment, the rhamnolipid producing microorganism is a bacterium of the Pseudomonadacae family. In an even further embodiment, the rhamnolipid-producing microorganism is a bacterium of the *Pseudomonas* genus, such as *P. alcaligenes*, *P. aeruginosa*, *P. chlororaphis*, *P. clemancea*, *P. collierea*. *P. fluorescens*, *P. luteola*, *P. putida*, *P. stutzeri* and *P. teessidea*. In a further embodiment, the rhamnolipid-producing microorganism is *P. aeruginosa*.

Culture (Fermentation) Medium

The rhamnolipid containing microorganism is cultured in culture (also referred to as fermentation) medium. Said culture medium comprises at least two carbon sources, at least one nitrogen source, at least one phosphorous source, at least one sulfur source, at least one sodium source, at least one magnesium source, at least one potassium source, at least one sulfur source and at least one chloride source.

The carbon source, in a particular embodiment, may be a sweetener and an oil containing one or more medium chain and/or long chain triglycerides (also referred to herein as medium chain containing triglyceride oil and long chain triglyceride containing oil respectively. In a more particular embodiment, each sweetener may be present in an amount of about 0.1% to about 2% w/v and/or each oil maybe present in the amount of about 3% to about 15% w/w, particularly, between about 4% to about 10% w/w, and more particularly, between about 6% and about 12% w/w.

The sweetener may be a refined or unrefined sweetener. Examples of refined sweeteners may include but are not limited to sucrose (table sugar) and *stevia*. The unrefined sweetener may be derived from sugar processing and/or from sap, one or more roots, fruit, one or more seeds, one or more nectars, one or more flowers, one or more leaves, one or more trees, one or more stalks, and/or one or more animals. In a more particular embodiment said unrefined sweetener used may be at least one of molasses, rice or barley malt syrup, nectar, yacon syrup, sugar beet syrup, corn syrup, sorghum syrup, maple syrup, palm sugar, or sweetener derived from potatoes or sweet potatoes. In a most particular embodiment, the unrefined sweetener is molasses. In another embodiment, the carbon source may further comprise a monosaccharide, e.g. glucose, a disaccharide, e.g. sucrose, a sugar alcohol, e.g. glycerol, a long chain alkane, e.g., n-hexadecane, a fatty acid such as caprylic acid (also termed octanoic acid), or mixtures thereof, organic acids (e.g. lactic acid, acetic acid, citric acid, propionic acid), alcohols (e.g. ethanol), and mixtures of these.

In one particular embodiment, the oil is medium chain triglyceride containing oil which may be commercially available medium chain triglyceride oil, which may contain a mixture of coconut oil, palm oil and/or other medium chain triglycerides (e.g. containing caprylic acid), coconut oil or palm oil. The long chain triglyceride may be soybean oil, canola oil, sunflower oil, safflower oil, peanut oil, hempseed oil, jatropha oil, calabash oil, linseed oil, corn oil, poppyseed oil, evening primrose oil, olive oil. In one embodiment, the long chain triglyceride contains fatty acids having an aliphatic tail of more than 13 carbon atoms; in a particular embodiment, it contains fatty acids having an aliphatic tail of between 13-21 carbon atoms.

In a particular embodiment, the oil may be a vegetable oil. The vegetable oil may be soybean oil, safflower oil, peanut oil, hempseed oil, canola oil, jatropha oil, calabash oil, linseed oil, corn oil, poppyseed oil, evening primrose oil, olive oil, palm kernel oil, palm oil, rapeseed oil, sesame oil, sunflower oil, grapeseed oil, walnut oil, wheat germ oil, or a combination of vegetable oils.

In a more particular embodiment, the long-chain triglyceride may be a vegetable oil and the sweetener may be an unrefined sweetener.

In another particular embodiment, the medium or long-chain triglyceride may be a vegetable oil where said vegetable oil is corn oil, canola oil or soybean oil or a medium chain triglyceride where the medium chain triglyceride is coconut oil and the sweetener is an unrefined sweetener which may be molasses, sugar beet syrup or sorghum syrup.

In a particular embodiment, the culture medium may comprise at least three carbon sources, wherein at least two of the carbon sources are sweeteners and at least one carbon source is an oil containing medium or long chain triglycerides. In an even more particular embodiment, at least two of the carbon sources are unrefined sweeteners and at least one carbon source is an oil containing medium chain triglycerides, e.g., coconut oil.

In another particular embodiment, the culture medium comprises at least four carbon sources, wherein at least two of the carbon sources are oils containing medium or long chain triglycerides and at least two carbon sources are sweeteners. In a more particular embodiment, at least one of the carbon sources is an oil containing medium chain triglycerides (e.g., coconut oil), one of the carbon sources is an oil containing long chain triglycerides (e.g., vegetable oil such as canola oil) and at least two carbon sources are unrefined sweeteners (e.g., molasses, sorghum syrup, sugar beet syrup).

The nitrogen source may be ammonium sulfate, ammonium phosphate, urea, yeast extract, meat extract, peptone, and corn steep liquor. In a particular embodiment, the nitrogen source is $NaNO_3$. In yet another embodiment, the nitrogen may be present in the amount of about 5-20 g/L.

The phosphorous source may, in a particular embodiment, be $H_3PO_4$ or $K_2HPO_4$. In yet another particular embodiment, said phosphorous is present in the amount of about 1-15 g/L.

The magnesium ion, in a particular embodiment, may be $MgSO_4*7H2O$ and/or $MgCl_2$. In a particular embodiment, the magnesium is present in the amount of about 0.2-2 g/L.

The potassium may be KCl and/or KOH. In a particular embodiment, the potassium is present in the amount of about 0.1 to about 2 g/L.

The sodium may be NaCl, $NaNO_3$, and NaOH. In a particular embodiment, said sodium ion is present in the amount of about 1-15 g/L.

The chloride may be KCl and NaCl. In a particular embodiment, said chloride ion is present in the amount of about 0.1-1 g/L.

The sulfur may be $H_2SO_4$. In a particular embodiment, said sulfur ion is present in the amount of about 0.1-1 g/L.

The sulfur and chloride sources may be derived from the aqueous layer waste stream, or also referred to as the aqueous liquid phase or aqueous phase of an acid treated clarified fermentation broth obtainable using procedures described in the U.S. Pat. No. 9,884,883. In a specific embodiment, the rhamnolipids precipitate out of solution from an acid treated clarified fermentation broth and form a solid phase and an oily liquid phase at the bottom and an aqueous liquid phase is generated at the top of the vessel used for this step. The aqueous liquid phase is removed using procedures known in the art and in a specific embodiment using methods set forth above (e.g., filtration, or centrifugation or settling combined with decanting). The above-referenced aqueous layer is a source of sulfur or chloride (depending upon the type of acid used during this pH adjustment of about 1.5 to 2.5, preferentially, about 2.05 to about 2.15 and is a source of micronutrients.

The culture medium may further comprise an emulsifier. In a particular embodiment, the emulsifier may include but is not limited to Arabic gum, guar gum and rhamnolipids. In yet another particular embodiment, the ratio of emulsifier to carbon source in said culture medium is between about 0.1% to about 20% w/w. In yet another particular embodiment, wherein said emulsifier may be present in the amount of about 0.1-2% by weight.

In a particular embodiment, the culture or fermentation medium is sterilized using methods known in the art. These methods may be filtration based, heat based, chemical based or ultraviolet light radiation based. In a particular embodiment, the heat based treatment may be via moist heat sterilization, particularly autoclaving.

In one embodiment, the culture medium (e.g., fermentation medium) may be sterilized by one of the above procedures. In another embodiment, the fermentation media may be sterilized by more than one of the procedures set forth above and these sterilizations could be in any order. It may be sterilized in the fermentation during the first cycle of fermentation, but should be sterilized in another vessel in subsequent cycles.

Micronutrient Composition

As noted above, said method may further comprise adding a micronutrient solution or composition. Said micronutrient may be a trace of Fe, Mn, Zn, Cu, Na. In a particular embodiment, said micronutrient is a Fe, Mn, Zn, Na or Cu salt. In a more particular embodiment said micronutrient composition comprises Fe, Mn, Zn, Na and Cu salts. The composition may be sterilized by filtration.

In particular embodiments, said Cu salt is at least one of $CuCl_2.2H_2O$ and $CuSO_4.5H_2O$ and may be present in the amount of about 0.5-3 g/L of micronutrient solution; said Mn salt is at least one of $MnSO_4.H_2O$ and $MnCl_2.4H_2O$ and may be present in the amount of about 0.1-2 g/L of micronutrient solution; said Zn salt is $ZnSO_4.7H_2O$ or $ZnCl_2$ and may be present in the amount of about 0.5-3 g/L of micronutrient solution; said Fe salt is at least one of $FeCl_3.6H_2O$ or $FeSO_4$ and may be present in the amount of about 0.1-1 g/L of micronutrient solution; said sodium salt is $Na_3C_6H_5O_7.2H_2O$ and may be present in the amount of about 1-5 g/L of micronutrient solution.

EXAMPLES

Example 1: 6% Soybean Oil Semi-Continuous Fermentation of Rhamnolipids with Unsulfured Blackstrap Sugar Cane Molasses Additive and Gum Arabic as an Emulsifier The fermentation of rhamnolipids is performed in a 10 L fermenter vessel (Labfors 5, Infors HT, Switzerland) with a working volume of 7.5 L. The fermentation media contains emulsified oil and nutrient solution in a balance of deionized (DI) water. First, 1.5 L of 8% emulsified soybean oil with 0.8% gum Arabic used as an emulsifier is prepared using a kitchen blender. With molasses addition (sulfur-free black-strap molasses, Golden Barrel, USA), molasses is added into the emulsified oil at 1%, 0.5% or 0.25% w/v prior to sterilization in an autoclave at 121° C. for 50 min. After it cools down to 37° C., 0.2 micron sterilized filtered nutrient solution containing 9.69 g/L 85% $H_3PO_4$, 5.21 g/L NaOH, 1 g/L $MgSO_4.7H_2O$, 1 g/L KCl and 15 g/L $NaNO_3$ is added. All chemicals are at least 99% purity except 85% $H_3PO_4$. $H_2SO_4$ is used to adjust the pH of the fermentation media to 6.3 prior to the inoculation with 2.5% R4 culture obtained from Example 3 of U.S. application Ser. No. 15/611,045, filed Jun. 1, 2017.

Fermentation is conducted at 37° C., 0.14 vvm air feed rate and 300-650 rpm agitation speed to maintain the dissolved oxygen (DO) at least 15%. When the agitation speed reaches 650 rpm but % DO is still below 15%, pure oxygen is added in along with air to keep the total gas flow rate constant (0.14 vvm). Approximately 20% of micro-trace element composition prepared according to an Example 2 listed in U.S. application Ser. No. 15/146,508, published as US20160326561 is continuously added in the fermenter at 80 ml/day using a peristatic pump. Silicon based antifoam (Snapsil FD30, BRB, Netherlands) is automatically added to knock down the foam during the fermentation. The fermentation occurs without pH control unless the pH exceeds 7.9. At this point, 25% $H_2SO_4$ is automatically added in to control the pH at 7.9.

After the fermentation is completed, about 77% fermentation broth (5.8 L) is drawn out while maintaining % DO at 15% (i.e., agitation and gas fed are still on) using a pump. A freshly sterilized 5.8 L of 8% emulsified oil culture media prepared in a separated container as mentioned in the first paragraph of this example is fed in the fermenter as a new feedstock. This process called "Draw and Fill (DF)" is disclosed in U.S. application Ser. No. 15/146,508, published as US20160326561. The first of 77% fermentation broth removed from the fermenter after inoculation is referred as batch DF0. Subsequently, the next fermentation broth being drawn out from the fermenter after the DF0 is called DF1 and so forth.

A trend of pH over the course of fermentation for DF1 (no molasses), DF5, 6 and 7 (0.5% molasses addition) shown in FIG. 1 demonstrates a 3 phase pattern of pH changes. First, the pH rapidly increases at the beginning of the fermentation. Second, the pH remains stable or slightly decreases prior to reach the $3^{rd}$ phase in which the pH increases again. The $2^{nd}$ phase is shortened with molasses addition. At the $3^{rd}$ phase, pH rises rapidly along with an increase in % DO while the agitation and air flow remain constant which indicating the fermentation is completed. Clear supernatant with no oil layer at the top is obtained after the removed fermentation broth is centrifuged at 9500 rpm for 10 min or 14,000 rpm at 5 min. The clear RL supernatant obtained from each DF is then sterilized and centrifuged again to obtain clarified broth (CB) which is filtered at 0.2 micron prior to being diluted with DI water at least 100-200 times depending upon the starting concentration of the material. The diluted samples are then injected into HPLC-ELSD (detail methodology shown in Example 2) for rhamnolipid quantification.

The fermentation results with various concentrations of molasses addition are shown in Table 2. The fermentation had been continuously run for 18 days with this "draw and fill" process generating over 65 L of fermentation broth using a 10 L fermenter vessel without shutting it down. The results in Table 2 clearly show that the addition of molasses shortens the fermentation time, mainly during the $2^{nd}$ phase of pH change (FIG. 1) yielding higher RL productivities compared to those without molasses, regardless of molasses concentration. This could also be due to an increase in bacterial cell mass depicted in g CDW/L (g cell dried weight/L) column.

TABLE 2

RL fermentation performance with 6% soybean oil with and without molasses

| DF# | % Molasses addition | Fermentation time (h) | RL (g/L) | RL Productivity (g/L/h) | g CDW/L | % Soybean oil consumption |
|---|---|---|---|---|---|---|
| DF0* | 0% | 76 | 75 | 1.0 | 16 | 90% |
| DF1 | 0% | 50 | 67 | 1.3 | 17 | 92% |
| DF2 | 1% | 38 | 72 | 1.9 | 32 | 96% |
| DF3 | 1% | 34 | 69 | 2.0 | 37 | 94% |
| DF4 | 1% | 36 | 69 | 1.9 | 37 | 95% |
| DF5 | 0.50% | 28 | 59 | 2.1 | 36 | 94% |
| DF6 | 0.50% | 28 | 60 | 2.2 | 31 | 93% |
| DF7 | 0.50% | 28 | 63 | 2.2 | 36 | 94% |
| DF8 | 0.25% | 33 | 63 | 1.9 | 28 | 91% |
| DF9 | 0.25% | 34 | 62 | 1.8 | 25 | 93% |
| DF10 | 0.25% | 34 | 65 | 1.9 | 22 | 95% |

*8% soybean oil was used.

Example 2: Quantification and Structure of Rhamnolipid Analysis

An Agilent 1260 Infinity high pressure liquid chromatography (HPLC) system equipped with 1290 Infinity evaporative light scattering detector (ELSD) and a reversed phase column, Pinnacle DB C18 (100×2.1 mm, 3 micron part #9414312) by Restek is used to quantify the concentration of rhamnolipids in the samples. The column temperature is held constant at 40° C. The sample injection volume is 25 µL. The mobile phase contains an equal volume of 5 mM ammonium acetate and acetonitrile at 0.25 ml/min. The nebulized and evaporator temperatures are at 40° C. with 1.7 SLM of nitrogen. The RL concentration is calculated using the dilution factor and the known concentration of the standards (i.e., the calibration curves of pure di-rhamnolipids and pure mono-rhamnolipids) obtained in house using a thin-layer chromatography.

The structure of rhamnolipids is analyzed using a Waters Corporation 2695 Separations Module connected to a Waters ZQ2000 single quadrupole mass spectrometer with electrospray ionization (LC/MS). The LC column is the same as that used in the HPLC set up. Injection volume is 5 µL. Mobile phases consists of 5 mM ammonium acetate (A) and acetonitrile (B). The flow rate is 0.2 mL/min having A=60% (B=40%) for 2 min then gradient to 100% B at 15 min where it is held for the remainder of the LC treatment. The samples are kept at 4° C. and the column temperature is held constant at 40° C. The LC/MS conditions for detection of rhamnolipids are listed in the Table 3 below.

TABLE 3

The LC/MS conditions

| Parameter | Setting |
|---|---|
| Capillary (kV) | 3.2 |
| Cone (V) | Per Ion |
| Extractor (V) | 5 |
| Source Temp (° C.) | 100 |
| Desolvation Temp (° C.) | 300 |
| Desolvation Gas (L hr$^{-1}$) | 250 |
| Cone Gas (L hr$^{-1}$) | 50 |

Example 3: RL Semi-Continuous Fermentation of 7.8% Soybean Oil and 0.5% Unsulfured Blackstrap Sugar Cane Molasses with Rhamnolipids as an Emulsifier The fermentation conditions, media and nutrient compositions are the same as shown in Example 1 except that purified rhamnolipid produced from Example 1 is used as an emulsifier. The carbon feedstock is 7.8% soybean oil with 0.5% unsulfured blackstrap molasses. The purified rhamnolipid is added to culture media as an emulsifier at the beginning with the freshly sterilized culture media.

The rhamnolipid (RL) concentration and productivity are shown in Table 4. Since RL is added in the media at the beginning as an emulsifier at 0.5% for DF0 and 0.1% for DF1-DF3, those amounts are subtracted out and the actual RL concentration produced from fermentation is reported as the adjusted RL (g/L).

TABLE 4

RL fermentation performance with 7.8% soybean oil and 0.5% molasses

| Batch | % RL as an emulsifier | Adjusted RL (g/L) | Fermentation (h) | RL Productivity (g/L/h) | % C in oil to C in RL |
|---|---|---|---|---|---|
| DF0 | 0.5% | 78 | 44 | 1.8 | 80% |
| DF1 | 0.1% | 90 | 35 | 7.6 | 92% |
| DF2 | 0.1% | 93 | 34 | 2.7 | 95% |
| DF3 | 0.1% | 80 | 33 | 2.4 | 87% |

It is worthwhile to note that the fermentation will take longer for the DF0 since the micro-organism needs time to adjust to the new environment from shake flask containing LB broth to the fermenter containing soybean oil. All the RL productivity of DF0 shown are lower than those obtained from DF1+. This is also an advantage of the semi-continuous fermentation process since the RL productivity and fermentation process efficiency increases after the first inoculation (DF0). Batch fermentation process will suffer from this lag every time the new batch starts since the fermentation has to start from the beginning (i.e., fresh inoculation for each batch).

% Carbon conversion is calculated based on the amount of carbon contained in soybean oil converted to carbon in rhamnolipids. The LC/MS results showed the rhamnolipid samples contains predominately mono- and di-rhamnose with C10-C10 and C10-C12 tails. Based on that result, the calculated carbon conversion from soybean oil to rhamnolipid production is greater than 80%.

Example 4: RL Semi-Continuous Fermentation of 8.8% Corn Oil with 0.5% Unsulfured Blackstrap Sugar Cane Molasses The fermentation conditions, media and nutrient compositions are the same as shown in Example 1 except that purified rhamnolipid produced from Example 1 is used as an emulsifier and 7.5 ml micro-trace elements are added daily. The carbon feedstock is 8.8% corn oil with 0.5% unsulfured blackstrap molasses and the purified rhamnolipid is added in culture media as an emulsifier at the beginning of the DF0 only at 0.1%. No rhamnolipid is added as an emulsifier for DF1-DF5.

TABLE 5

RL fermentation performance with 8.8% corn oil and 0.5% molasses

| Batch | Adjusted RL (g/L) | Fermentation time (h) | RL Productivity (g/L/h) | % Mono RL |
|---|---|---|---|---|
| DF1 | 106 | 46 | 2.3 | 55% |
| DF2 | 93 | 45 | 2.1 | 54% |
| DF3 | 106 | 51 | 7.1 | 58% |
| DF4* | 82 | 40 | 2.1 | 53% |
| DF5 | 97 | 49 | 2.0 | 60% |

*7.8% corn oil is used.

The RL productivity obtained from the fermentation of corn oil is as good as those from soybean oil. The RL productivity is in the range of 2-2.3 g RL/L/h.

Example 5: Shake Flask Experiments with Sugar Beet and Sorghum Syrups at Various Concentrations The shake flask experiment is performed at 37° C., 250 rpm using a MaxQ™ 8000 Stackable Orbital Shakers (Thermo Scientific) in 250 ml Pyrex Erlenmeyer baffle flasks. Each flask contained 40 ml of culture medium containing 8% soybean oil with nutrient composition the same as described in Example 1 but without micro-trace elements. The baffle flasks are autoclaved at 121° C. for 20 min and being cooled down to room temperature prior to 2.5% v/v inoculation with P. aeruginosa culture. The samples are collected at 68, 92 and 116 h using sterilized pipets. The samples are centrifuged at 14,000 rpm for 5 min to obtain clear supernatant (no oil layer) which is then sterilized and filtered at 0.2 micron prior to dilution for RL concentration analysis using the HPLC/ELSD.

The sample without clear supernatant (i.e., with oil layer on top) is denoted as "No CB" meaning that it was not injected to HPLC due to too high oil concentration in the sample. The results shown in Table 6 clearly show that the rhamnolipid production is also enhanced by the addition of sugar beet syrup and sorghum syrup.

TABLE 6

Rhamnolipid concentration with sugar beet and sorghum syrups sugar

| Flask (h) | No additive | Sugar beet syrup | | | Sorghum syrup | | |
|---|---|---|---|---|---|---|---|
| | | 0.50% | 1% | 1.50% | 0.50% | 1% | 1.50% |
| 68 | No CB | No CB | No CB | No CB | No CB | No CB | 74 |
| 92 | No CB | 72 | 84 | 80 | No CB | 90 | 103 |
| 116 | 56 | 71 | 77 | 80 | 88 | 85 | 91 |

Example 6: RL Batch Fermentation with 8% Soybean Oil and 0.5% Unsulfured Blackstrap Sugar Cane Molasses The fermentation conditions, media and nutrient compositions are the same as shown in Example 4 except that this is a batch fermentation meaning that the fermentation is started with R4 inoculation (time=0) and once the fermentation is completed, the fermentation is shut down and cleaned. The carbon feedstock is 8% soybean oil with 0.5% unsulfured blackstrap molasses. The purified rhamnolipid is added in culture media as an emulsifier at 0.1% with the freshly sterilized culture media.

The fermentation takes 44 h to complete. The rhamnolipid (RL) concentration is obtained at 88 g/L in 44 h and thus the RL productivity is 1.9 g/L/h compared to 1 g/L/h obtained in DF0 shown in Example 1 with no molasses addition.

Example 7: RL Semi-Continuous Fermentation of 8% Coconut Oil and 0.5% Unsulfured Blackstrap Sugar Cane Molasses with Rhamnolipids as an Emulsifier The fermentation conditions, media and nutrient compositions are the same as shown in Example 3 except that the carbon feedstock is 8% coconut oil. No rhamnolipid is added as an emulsifier for DF1-DF4 since it is generated from DF0. The fermentation time is consistent at 32-36 h with 0.5% molasses addition.

TABLE 8

RL fermentation performance with 8% coconut oil and 0.5% molasses

| Batch | RL (g/L) | Fermentation time (h) | RL Productivity (g/L/h) | % Mono RL |
|---|---|---|---|---|
| DF0 | 68 | 38 | 1.8 | 66% |
| DF1 | 75 | 33 | 2.2 | 63% |
| DF2 | 74 | 33 | 2.3 | 64% |
| DF3 | 74 | 32 | 2.3 | 62% |
| DF4 | 75 | 36 | 2.1 | 61% |

Example 8: RL Fermentation of 8% Coconut Oil with Combination Sugar Additives The fermentation conditions, media and nutrient compositions are the same as shown in Example 7 except that the sugar additives are unsulfured blackstrap sugar cane molasses, sorghum syrup and sugar beet syrup.

TABLE 9

RL fermentation performance with 8% coconut oil and various sugar additives

| Sugar | RL (g/L) | Fermentation time (h) | RL Productivity (g/L/h) | % Mono RL |
|---|---|---|---|---|
| No sugar | 91 | 88 | 1.0 | 57% |
| 0.25% Molasses + 0.25% Sorghum | 79 | 33 | 2.4 | 63% |
| 0.25% Molasses + 0.25% Sugar beet | 80 | 35 | 2.3 | 60% |
| 0.25% Sugar beet + 0.25% Sorghum | 82 | 57 | 1.4 | 56% |
| 0.5% Sugar beet + 0.5% Sorghum | 81 | 41 | 2.0 | 59% |

Example 9: RL Fermentation of Medium and Long Chain Triglyceride Oils with 0.5% Unsulfured Blackstrap Sugar Cane Molasses The fermentation conditions, media and nutrient compositions are the same as shown in Example 7 except that 4% coconut and 4% canola oils representing medium and long chain triglyceride oils, respectively, are used as a feedstock with 0.5% molasses. The fermentation is completed in 32 h with RL concentration of 88 g/L and thus, the RL productivity is at 2.8 g/L/h.

REFERENCES

1. Müller, M. M., et al., *Rhamnolipids—Next generation surfactants?* Journal of Biotechnology, 2012. 162(4): p. 366-380.
2. Sekhon Randhawa, K. K. and P. K. S. M. Rahman, *Rhamnolipid biosurfactants—past, present, and future scenario of global market.* Frontiers in Microbiology, 2014. 5: p. 454.
3. Wittgens, A., et al., *Growth independent rhamnolipid production from glucose using the non-pathogenic Pseudomonas putida KT2440.* Microbial Cell Factories, 2011. 10(1): p. 1-18.
4. Banat, I. M., et al., *Cost effective technologies and renewable substrates for biosurfactants' production.* Frontiers in Microbiology, 2014. 5: p. 697.
5. Kaskatepe, B. and S. Yildiz, *Rhamnolipid Biosurfactants Produced by Pseudomonas Species.* Brazilian Archives of Biology and Technology, 2016. 59.
6. Desai, R. M. P. a. A. J., *Biosurfactant production by Pseudomonas aeruginosa GS3 from molasses.* Letters in Applied Microbiology, 1997. 25: p. 91-94.
7. Onbasli D., A. B., *Biosurfactant production in sugar beet molasses by some Pseudomonas spp.* J Environ Biol., 2009. 30(1): p. 161-163.
8. Gudiña, E. J., et al., *Valorization of agro-industrial wastes towards the production of rhamnolipids.* Bioresource Technology, 2016. 212: p. 144-150.
9. Rashedi, H., et al., *Environmental importance of rhamnolipid production from molasses as a carbon source.* International Journal of Environmental Science & Technology, 2005. 2(1): p. 59-62.
10. Giani, C., et al. *Pseudomonas aeruginosa and its use in a process for the biotechnological preparation of L-rhamnose.* U.S. Pat. No. 5,501,966 A, 1996.
11. Li, A.-h., et al., *Rhamnolipid Production by Pseudomonas Aeruginosa GIM 32 Using Different Substrates Including Molasses Distillery Wastewater.* Applied Biochemistry and Biotechnology, 2011. 163(5): p. 600-611.
12. Gong, Z., Y. Peng, and Q. Wang, *Rhamnolipid production, characterization and fermentation scale-up by Pseudomonas aeruginosa with plant oils.* Biotechnology Letters, 2015. 37(10): p. 2033-2038.
13. Zhu, L., et al., *Enhanced rhamnolipids production by Pseudomonas aeruginosa based on a pH stage-controlled fed-batch fermentation process.* Bioresource Technology, 2012. 117: p. 208-213.

The invention claimed is:

1. A semi-continuous fermentation method for producing rhamnolipids (RL), said method comprising:
   (a) culturing a rhamnolipid-producing microorganism in a culture medium comprising:
   i. at least two carbon sources, wherein a first carbon source is a sweetener and a second carbon source is an oil containing medium or long chain triglycerides;
   ii. at least one nitrogen source;
   iii. at least one phosphorous source;
   iv. at least one magnesium source;
   V. at least one potassium source;
   vi. at least one sulfur source;
   vii. at least one chloride source; and
   viii. at least one sodium source wherein said culture medium comprises between about 0.1% to about 2.0% by weight of said sweetener (w/v) in said culture medium and between about 3-15% by weight of said oil (w/v) in said culture medium;

wherein said rhamnolipid-producing microorganism is cultured in said culture medium for at least about 1 day to obtain a first fermentation medium comprising the rhamnolipids and the rhamnolipid-producing microorganism;

(b) removing at least about 70% of said first fermentation medium obtained in step (a);

(c) replacing said first fermentation medium removed in (b) with culture medium having the composition set forth in step (a);

(d) repeating steps (a)-(c) at least one time to obtain a subsequent fermentation medium comprising the rhamnolipids and the rhamnolipid-producing microorganism;

wherein said culturing step (a) yields rhamnolipids at a rate of at least about 1.7 g/L/h; and wherein said method yields a rhamnolipid titer of at least about 40 g/L.

2. The method of claim 1, wherein said rhamnolipid-producing microorganism is cultured in step (a) for about 1 to about 4 days.

3. The method of claim 1, further comprising adding a micronutrient composition comprising one or more micronutrients at a concentration of no more than 20 mg/L of micronutrient composition to said culture medium in step (a) at 0.1% v/v of total fermentation volume per day.

4. The method of claim 1, wherein said first fermentation medium or said subsequent fermentation medium is removed in step (b) during agitation and while maintaining air flow.

5. The method of claim 4, wherein said air flow is oxygen enriched air.

6. The method of claim 1, wherein there is no sedimentation step between steps (a) and (b).

7. The method of claim 1, wherein said semi-continuous fermentation is sustained for at least about 20 days.

8. The method of claim 1, wherein said rhamnolipid-producing microorganism is a *Pseudomonas* microorganism.

9. The method of claim 8, wherein said *Pseudomonas* microorganism is *Pseudomonas aeruginosa*.

10. The method of claim 1, wherein said sweetener is an unrefined sweetener and/or said oil is a vegetable oil.

11. The method of claim 10, wherein said unrefined sweetener is derived from sap, one or more roots, fruit, one or more seeds, one or more trees, or one or more animals.

12. The method of claim 1, wherein said sweetener is at least one of molasses, rice or barley malt syrup, nectar, yacon syrup, sugar beet syrup, sorghum syrup and/or said oil is at least one of soybean oil, safflower oil, peanut oil, hempseed oil, jatropha oil, coconut fat, calabash oil, linseed oil, corn oil, poppy seed oil, evening primrose oil, olive oil, palm kernel oil, palm oil, rapeseed oil, sesame oil, sunflower oil, grapeseed oil, walnut oil, wheat germ oil, coconut oil, or medium chain triglyceride oil.

* * * * *